United States Patent
Haase et al.

(10) Patent No.: US 9,671,339 B2
(45) Date of Patent: Jun. 6, 2017

(54) METHOD FOR DETERMINING A TURBIDITY AND TURBIDITY SENSOR FOR IMPLEMENTING THE METHOD

(71) Applicant: Endress + Hauser Conducta Gesellschaft für Mess—und Regeltechnik mbH + Co. KG, Gerlingen (DE)

(72) Inventors: Bjorn Haase, Stuttgart (DE); Matthias Grossmann, Vaihingen-Enz (DE); Carsten Gotz, Ettenheim (DE); Thilo Kratschmer, Gerlingen (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 0 days.

(21) Appl. No.: 14/958,012

(22) Filed: Dec. 3, 2015

(65) Prior Publication Data

US 2016/0161405 A1 Jun. 9, 2016

(30) Foreign Application Priority Data

Dec. 9, 2014 (DE) .......................... 10 2014 118 205

(51) Int. Cl.
| | | |
|---|---|---|
| *G01N 21/00* | (2006.01) | |
| *G01N 21/51* | (2006.01) | |
| *G01N 21/47* | (2006.01) | |

(52) U.S. Cl.
CPC ....... *G01N 21/51* (2013.01); *G01N 2021/473* (2013.01); *G01N 2021/4711* (2013.01); *G01N 2021/4726* (2013.01)

(58) Field of Classification Search
CPC .............. G01N 21/51; G01N 21/532; G01N 2201/062; G01N 21/53; G01N 15/06;
(Continued)

(56) References Cited

U.S. PATENT DOCUMENTS

| | | | |
|---|---|---|---|
| 2006/0061765 A1* | 3/2006 | Rezvani | G01N 21/51 356/442 |
| 2009/0059218 A1* | 3/2009 | Harner | G01N 21/4785 356/243.2 |

(Continued)

FOREIGN PATENT DOCUMENTS

| | | |
|---|---|---|
| DE | 10111006 A1 | 11/2002 |
| DE | 102013111416 A1 | 4/2015 |
| EP | 1238623 A2 | 9/2002 |

OTHER PUBLICATIONS

German Search Report, German Patent Office, Munich, DE, Sep. 16, 2015.

*Primary Examiner* — Michael P Stafira
(74) *Attorney, Agent, or Firm* — Mark A. Logan; PatServe

(57) ABSTRACT

A method for determining a turbidity of a medium in a container using at least one turbidity sensor. Depending on the ambient conditions at the installation location of the turbidity sensor, comprising the following steps: passing transmitted radiation through the medium, wherein the transmitted radiation is converted by interaction with the medium, as a function of the turbidity in the received radiation; receiving the received radiation; converting the received radiation into a scattered light intensity, and determining the turbidity from the scattered light intensity. The method is characterized by the following steps: detecting the chronological sequence of the scattered light intensity; determining a mean value on the basis of the chronological sequence of the scattered light intensity; determining the turbidity from the mean value using a calibration model by assigning a turbidity to each mean value; determining a corrected mean value on the basis of the chronological sequence of the scattered light intensity, by determining a noise parameter from the scattered light intensity, and by
(Continued)

determining the corrected mean value from the noise parameter using a noise model, and determining a corrected turbidity at least from the corrected mean value using the calibration model by assigning a corrected turbidity to each corrected mean value. The invention further relates to a turbidity sensor for implementing the method.

14 Claims, 2 Drawing Sheets

(58) Field of Classification Search
CPC ........... G01N 2015/0693; G01N 33/18; G01N 33/86; G01N 2021/4711; G01N 2021/4726; G01N 2021/513; G01N 21/59; G01N 21/645; G01N 21/65
See application file for complete search history.

(56) References Cited

U.S. PATENT DOCUMENTS

| | | | |
|---|---|---|---|
| 2011/0043807 A1* | 2/2011 | Andelic | G01N 21/49 356/441 |
| 2012/0162645 A1* | 6/2012 | Andelic | G01N 21/49 356/338 |
| 2013/0016354 A1* | 1/2013 | Wu | G01N 21/53 356/441 |
| 2015/0103344 A1 | 4/2015 | Kratschmer | |
| 2015/0198534 A1* | 7/2015 | Sinfield | G01N 21/65 356/301 |

* cited by examiner

20
METHOD FOR DETERMINING A TURBIDITY AND TURBIDITY SENSOR FOR IMPLEMENTING THE METHOD

TECHNICAL FIELD

The invention relates to a method for determining a turbidity of a medium in a container using at least one turbidity sensor. The invention further relates to a turbidity sensor for implementing the method.

BACKGROUND DISCUSSION

Any light striking particles suspended in a liquid is scattered. The intensity of this light scattering is used in the visual turbidity measurement as a direct measure of the turbidity determination. In general, the light is guided through optical windows along its path from the light source to the medium to be measured as well as from the medium to the photodetector after light scattering, for example at a particle.

The measured scattered light intensity can be substantially negatively affected by the following two interference variables:

First, by reflections at walls and objects: The measuring signal is falsified if the light emitted from the sensor is reflected at walls or other objects or scattered at walls or other objects, and if these reflection and/or scattered signals that are not caused by suspended particles are detected by the sensor. This occurs, for example, in restricted installation spaces such as the measurement in pipes or fittings, or at very low turbidity, i.e. at a low extinction.

Second, due to any dirt on the optical window: In the case of window contamination such as deposits, biofilms, or adhering air bubbles, it is possible that light is scattered on the dirt and falls directly on the photodetector, without the light being scattered by suspended particles. Nevertheless, the light absorption caused by window contamination may also decrease the scattered light intensity that is received at the photodetector. Both cases lead to a falsification of the measured value.

Detection and/or compensation of the interference variable has been implemented until now either by model-based diagnosis method (for this, refer to German Patent, DE 10 2009 001 929 A1) or by multi-beam alternating light. Both methods require a plurality of light sources and/or photodetectors. However, this is not possible for many applications or does not comply with regulations, e.g. DIN ISO 7027 or EPA 180.1, which specify a single light source, a single photodetector and light intensity measurement at 90° for single light beam.

SUMMARY OF THE INVENTION

The object of the invention is to provide a low-maintenance optical sensor and a corresponding method that performs detection and compensation of an interference variable, wherein the method and the sensor should be applicable even for optical single-beam sensors.

The object is achieved by a method comprising the steps of: passing the transmitted radiation through the medium, wherein the transmitted radiation is converted by interaction with the medium, in particular by scattering, as a function of the turbidity in the received radiation; receiving this radiation; converting the received radiation into a scattered light intensity, and determining the turbidity from the scattered light intensity. The method is characterized by the steps of: detecting the chronological sequence of the scattered light intensity; determining a mean value on the basis of the chronological sequence of the scattered light intensity; determining the turbidity from the mean value using a calibration model by assigning a turbidity value to each mean value; determining a corrected mean value on the basis of the chronological sequence of the scattered light intensity, by determining a noise parameter from the scattered light intensity, and by determining the corrected mean value from the noise parameter using a noise model, and determining a corrected turbidity at least from the corrected mean value using the calibration model by assigning a corrected turbidity to each corrected mean value.

Optical turbidity measurement is a measurement characterized by considerable noise. This is understandable especially at a very low turbidity range: The measured signal is very low if the photodetector does not "see" any light-scattering particles. If, however, light scattering takes place at a suspended particle in the viewing range of a photodetector, the detected signal intensifies rapidly before the particle disappears from the viewing range of the photodetector and the signal fades again. Thus, statistical fluctuations in the number of particles in the viewing range of the photodetector generate a statistical noise component in the measured signal, wherein the noise is associated with the movement of the particles in the medium. Interference signals, which are generated by, e.g. slowly forming contamination or constant scattered light reflections in fittings are characterized by a different noise. By evaluating the noise, a distinction can be made between parts that are correlated with turbidity and the undesired interference signal parts of the scattered light intensity.

In one embodiment, the corrected turbidity is determined from the corrected mean value and the mean value.

Preferably, the method further comprises the step of: comparing the turbidity with the corrected turbidity and making a statement about the reliability or unreliability of the turbidity if the turbidity coincides with the corrected turbidity or not based on the comparison. Thus, a statement can be made about the reliability of the measurement.

For a given medium, each measured scattered light intensity, and thus, each mean value of the scattered light intensity can be assigned to a predicted noise value, namely a predicted value of the noise parameter. One speaks of a noise that is characteristic of the measurement. value. In optical turbidity measurements, this noise parameter increases with the measured value.

This relationship can be determined in a first advantageous variant under standard conditions. Standard conditions in this case refer to a measurement in the laboratory at constant temperature, constant barometric pressure, well-defined amount of medium and regular stirring of the medium to keep the turbidity constant. In another advantageous variant, this relationship is determined directly in the process. By an appropriate type of installation and cleaning, it must be ensured that the two interference variables of wall effects and contamination are not present and therefore, do not affect the measured value and the noise variable.

In another advantageous embodiment, the method further comprises the step of: If the turbidity is not identical to the corrected turbidity, compensation of the turbidity by determining the actual turbidity from the corrected turbidity. In other words, the actual turbidity is not determined using the (directly measured) mean value of turbidity, but the calculated noise parameter is converted to a corrected mean value and the corresponding turbidity is determined with this, since the noise is characteristic of the specific turbidity (scattered light intensity).

Alternatively, in another preferred embodiment, the corrected turbidity is determined using the (measured) mean value and the corrected mean value.

Both variants can be implemented using a two-dimensional lookup table, wherein an output variable (corrected turbidity) is determined from two input variables (mean value and corrected mean value).

In another advantageous further development, the noise parameter is determined by a frequency analysis, in particular by a Fourier transformation of the chronological sequence of the scattered light intensity, or the noise parameter is determined using a statistical method, e.g. calculating the standard deviation of the scattered light intensity. Both are mathematical methods that are relatively easy to implement.

Preferably, the corrected mean value is determined from the noise parameter by means of a noise model, $$RK = \alpha \cdot \sqrt{MW_{kor}} + \beta$$

where RK is the noise parameter, $\alpha$ is a scaling factor for the conversion of an electrical variable to turbidity, $MW_{kor}$ is the mean value of the scattered light intensity and $\beta$ is a constant for the turbidity sensor, wherein this requires solving the above formula to find the corrected mean value. The constant $\alpha$ is different for various measuring angles (e.g. turbidity measured at 90° or 135°) and optionally for different measurement media. The constant $\beta$ describes the equipment noise and depends on the relevant hardware, namely the corresponding turbidity sensor together with electronics, etc. Both parameters can be determined either theoretically ($\alpha$: scattered light analysis with reception- and detection characteristics of the sensor and scattering properties of the medium; $\beta$: noise analysis of the sensor) or practically by two-point calibration.

In an advantageous embodiment, the noise parameter depends on ambient conditions and/or the state of the turbidity sensor.

Preferably, the ambient conditions are at least materials, diameter, surface roughness, surface color, surface texture and/or deposits on the container, and/or distance of turbidity sensor to the container.

More preferably, the state of the turbidity sensor is surface texture, deposits, wear of an optical window, and/or contamination at the turbidity sensor.

In another advantageous further development, the method further comprises the step of: displaying the noise parameter and/or a message about the (interfering) ambient condition and/or (interfering) state of the turbidity sensor.

Based on the aforementioned assignment of the noise parameter to turbidity and the fact that the noise parameter depends on the ambient conditions and on the state of the turbidity sensor, a specific source of interference in the environment and/or on the sensor itself may be inferred from a determined noise parameter.

The object is further solved by a turbidity sensor for implementing a method as described above.

In another embodiment, the turbidity sensor comprises a higher-level unit, which determines the noise parameter, the mean value, the corrected mean value, the turbidity and/or the corrected turbidity and performs a comparison of the turbidity with the corrected turbidity, wherein the higher-level unit is part of the turbidity sensor or is installed in an external device, in particular a transmitter.

Preferably, the turbidity sensor is connected with the external device, in particular the transmitter, over an electrically insulated, and in particular, inductive interface, or the turbidity sensor is connected with the external device, in particular the transmitter, over a wireless, in particular a Bluetooth interface.

BRIEF DESCRIPTION OF THE DRAWINGS

The invention is further explained in more detail by means of the following figures. They show.

DETAILED DISCUSSION IN CONJUNCTION WITH THE DRAWINGS

Figure 1:
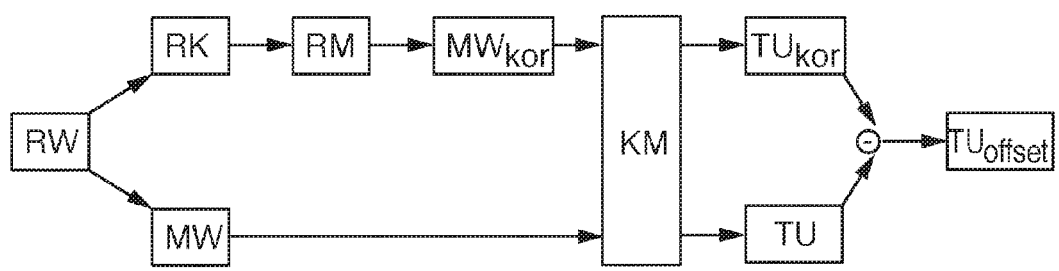
FIG. 1 is overview of the method according to the invention.

The reference symbols of similar features remain the same in the figures.

Turbidity measurement is an application of the method according to the invention. The turbidity measurement is only dealt with briefly as it is known in principle.

For measuring the turbidity, a light beam is directed through the medium and it is deflected there from its original direction by visually denser constituents, for example solid particles. This process is referred to as scattering. The incident light is scattered in many directions, i.e. at different angles to the direction of propagation. Here, several ranges of angles are of great interest, wherein two are explained here in detail: The scattered light that is detected at an angle of 90° opposite the direction of the incident light, or the scattered light intensity RW that is detected by the detectors, such as photodiodes, is only slightly influenced by the particle size. Another interesting scattering angle is 135° to the direction of the incident light. This light in the 135° direction also gives information at high particle densities. If the particle density in the medium is low, much light is scattered along the 90° path and little light along the 135° path. If the particle density increases, this phenomenon is inverse (more light along the 135° path, less light along the 90° path). A common turbidity sensor has two independent sensor units that are arranged in parallel. The application-dependent evaluation of the two signals results in stable measured values. Thus, the optimum measurement of turbidity and solids is possible: The 90° path is preferably used at low turbidity values. The 135° path is used at average and high turbidity values and at solid measurements.

The measurement method essentially includes four methods. The multi-beam alternating light method, 90° scattered light method, the forward scattered light method and the backward scattered light method.

The four-beam alternating light method, as a kind of multi-beam alternating light method is based on two light sources and two light receivers. LEDs with a long service life are used as monochromatic light sources. These LEDs that are alternately pulsed generate two scattered light signals at the receivers per LED pulse.

In the 90° scattered light method, the measurement is carried out at a wavelength of 860 nm as described in ISO 7027/EN 27027. The emitted light beam is scattered by the solid particles suspended in the medium. The so-generated scattered radiation is measured using scattered light receivers, which are arranged at an angle of 90° to the light sources. The turbidity of the medium is determined from the quantity of scattered light.

In the backscatter light method, the light beam transmitted is scattered in the medium by the solid particles. The generated backscatter is measured by the scattered light receiver. The turbidity of the medium is determined from the quantity of backscattered light. Very high turbidity values can be measured using this form of scattered light measurement.

The three measurement methods mentioned are the most common ones that are partly specified by standards. However, other methods and measuring angles may be specified, depending on the country.

The forward scattered light method, for example at an angle of 11°, is used less frequently However, all of the described methods face the problem described above that interference variables, e.g. reflections at the installation or contamination of the optical window, falsify the measurement result. The user must try to "eliminate" these undesired reflections "by calibration", but as mentioned, these tests are time and cost-intensive a well as prone to error.

FIG. 1 shows an overview of the method according to the invention. A noise parameter RK as well as the mean value are determined from the measured scattered light intensity RW (the "raw value", see above). More specifically, the noise parameter RK and the mean value MW are determined by a higher-level unit (not shown), for example in a microcontroller (see below). The higher-level unit may be part of the turbidity sensor, or installed in an external device, in particular a transmitter. If the higher-level unit is installed in a transmitter, the turbidity sensor is connected to the transmitter over an electrically insulated, in particular inductive, interface. If the higher-level unit is in an external unit, the external unit can be configured as a mobile phone, tablet, etc. Then, the communication is usually carried out wirelessly, e.g. by a Bluetooth connection. All calculations, regulations, control etc. are performed by the higher-level unit.

The noise parameter RK can be determined in various ways. The noise parameter RK may be determined by a frequency analysis, in particular a Fourier transformation of the chronological sequence of the scattered light intensity RW. Alternatively, the noise parameter RK can be determined using statistical methods such as the calculation of the standard deviation. The scattered light intensity RW is detected over its course of time. From this course of time, e.g. the arithmetic mean of ten consecutive values, namely a mean value MW is calculated by means of an algorithm.

Then, a corrected mean value $MW_{kor}$ is determined from the noise parameter RK by means of a noise model RM. The noise model RM is briefly described below. The $$RK = \alpha \cdot \sqrt{MW_{kor}} + \beta$$

corrected mean value $MW_{kor}$ is determined by means of the formula (solve the formula accordingly). Here, $\alpha$ is a scaling factor for the conversion of an electrical variable to the turbidity and $\beta$ is a specific constant for the turbidity sensor. The constant $\alpha$ is different for various measuring angles (e.g. turbidity measured at 90° or 135°). The constant $\beta$ describes the equipment noise and it depends on the relevant hardware, namely the corresponding turbidity sensor together with electronics, etc. Both parameters can be calculated practically by two-point calibration, $\alpha$ can be determined in a theoretical manner by means of light scattering analysis with reception- and detection characteristics of the sensor and scattering properties of the medium and $\beta$ by means of noise analysis of the sensor.

Figure 2:
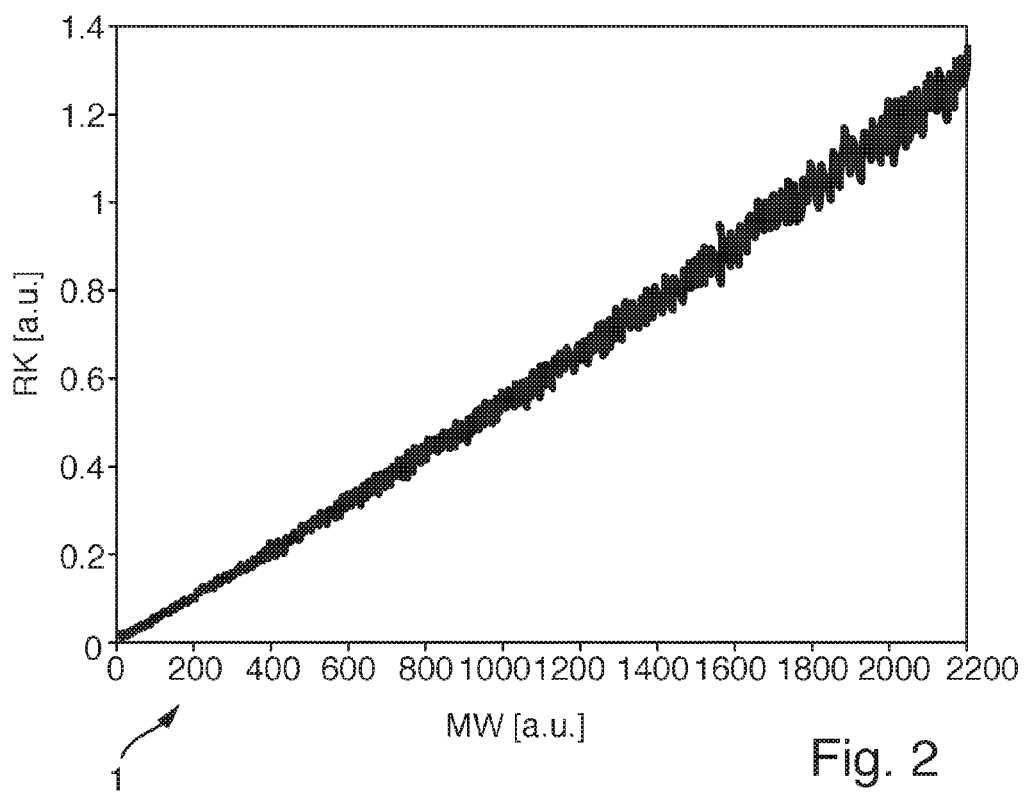
FIG. 2 is a diagram of assignment of the mean value of the scattered light intensity to the noise parameter.

In the next step, see FIG. 2, an (uncorrected) turbidity TU and a corrected turbidity $TU_{kor}$ are determined from both the mean value MW as well as the corrected mean value $MW_{kor}$ kor by means of a calibration model KM. Using the calibration model KM, a turbidity TU or a corrected turbidity $TU_{kor}$ is uniquely assigned to each mean value MW or each corrected mean value $MW_{kor}$. One possible implementation of the calibration model KM is a two-dimensional lookup table that assigns a turbidity value to the two input signals, namely mean value MW and corrected mean value $MW_{kor}$ kor by means of calibration points. The corrected turbidity $TU_{kor}$ can be determined from the (measured) mean value MW and the corrected mean value $MW_{kor}$. Alternatively, the corrected turbidity $TU_{kor}$ is only determined from the corrected mean value $MW_{kor}$. The turbidity TU is only determined from the mean value MW.

Then, the turbidity TU and the corrected turbidity $TU_{kor}$ are compared. From this comparison, by subtracting from each other (an offset of turbidity $TU_{offset}$ results) in the simplest case, a statement about the reliability or unreliability of the turbidity can be made as to whether the turbidity TU coincides with the corrected turbidity $TU_{kor}$ or not. There is a high reliability, for example, if the deviation $TU_{offset}$ is less than 1%. There is a low reliability, for example, if the deviation $TU_{offset}$ is more than 100%. If there is no correspondence, i.e. a deviation from a certain tolerance range, there is interference through an interference variable or source.

In another step, the turbidity can be corrected if the determined turbidity TU does not correspond to the corrected turbidity value $TU_{kor}$, i.e. the deviation $TU_{offset}$ exceeds a certain value. This is done by determining the actual turbidity using the corrected turbidity value $TU_{kor}$, i.e. ultimately based on the noise parameter RK and thus, on the basis of the noise.

As mentioned, using the calibration model KM, a turbidity value TU and a corrected turbidity value $TU_{kor}$ are uniquely assigned to each mean value MW or each corrected mean value $MW_{kor}$. The corrected mean value $MW_{kor}$ is also clearly determined from the noise parameter RK using the noise model RM. Therefore, turbidity TU and corrected turbidity $TU_{kor}$ act like the noise parameter RK and mean value MW.

FIG. 2 shows an assignment diagram 1 of the (measured) mean value MW to the noise parameter RK. The mean value MW corresponds to the turbidity value TU (see above), i.e. in FIG. 2, a certain value of the noise parameter RK is uniquely assigned to a particular turbidity value. In other words, each mean value MW is equivalent to a noise parameter RK, and vice versa. This assignment is stored in the turbidity sensor, for example in a memory in the higher-level unit. In FIG. 2 as well as in the following figures, the units and the corresponding numerical values are chosen in an exemplary and arbitrarily manner.

The value of the noise parameter RK forms a characteristic noise for the respective value. This characteristic noise may be determined at standard conditions, for example, in advance and not at the installation location of the turbidity sensor. Standard conditions in this case refer to a measurement in the laboratory at constant temperature, constant barometric pressure, well-defined amount of medium and regular stirring of the medium to keep the turbidity constant.

In general, the correlation between mean value MW and noise RK must be determined at conditions, where no interfering influences such as dirt or wall effects occur. This can be in the laboratory as mentioned, but also at the user's location. Likewise, the same applies to the α and β parameters mentioned above.

As mentioned, the turbidity value TU is compared to the corrected turbidity value $TU_{kor}$. The measurement appears to be okay if a correspondence occurs here. If there is no correspondence, i.e. a deviation from a certain tolerance range, there is interference through an interference variable or source. Ideally, this is detected and the turbidity sensor is accordingly compensated. This will be discussed in more detail below.

Upon occurrence of an interference variable, e.g. sensor "sees" a wall, the measured scattered light intensity RW increases, but the corrected average value $MW_{kor}$ determined therefrom remains approximately constant (see FIG. 3), as the wall acts rather like a mirror. By the measured scattered light intensity RW, the graph in FIG. 2 is expected to show a certain noise parameter or a specific corrected mean value, but another corrected mean value is actually found. Thus, an interference is detected. Moreover, a compensation can also be performed. This is illustrated in FIG. 3.

Figure 3:
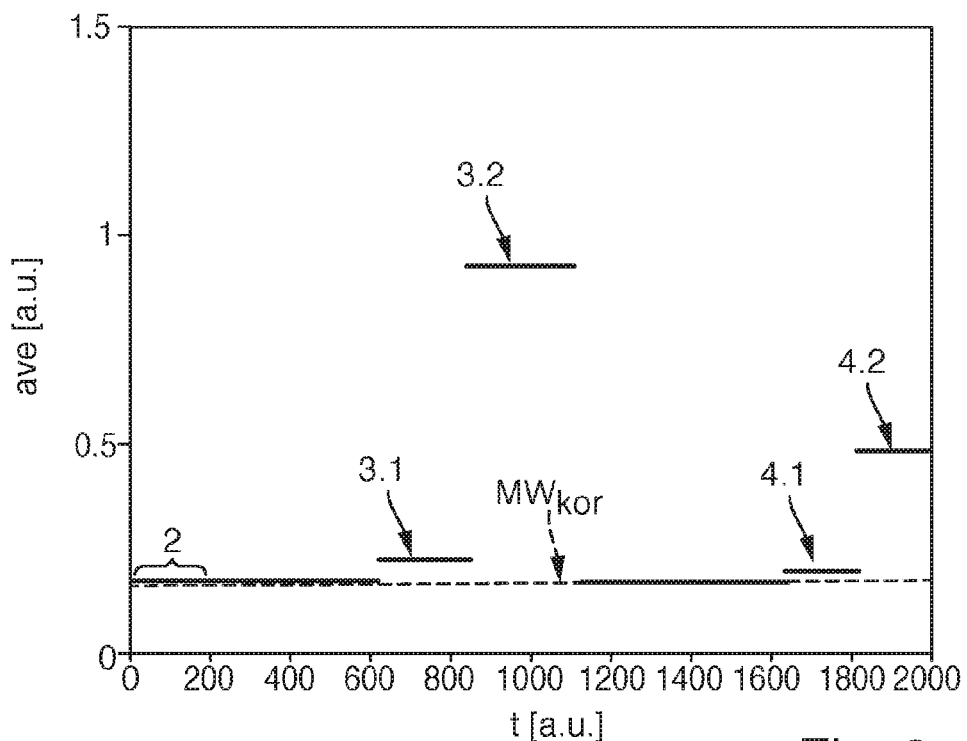
FIG. 3 is a chronological sequence of the determined and expected noise parameter upon change in the ambient conditions.

FIG. 3 shows turbidity measurements in a basin with tap water. In succession, i.e. the x-axis shows the time t, various interference sources were fed to the turbidity sensor. On the y-axis, mean values ave are plotted. Two different mean values ave are dealt with in the context of this invention. First, the corrected mean value $MW_{kor}$ and second, the other measured mean values, characterized in FIG. 2 with the reference numerals 3.1, 3.2, 4.1 and 4.2. Specifically, various wall effects were simulated by holding a stainless steel plate (reference numerals 3.1 and 3.2) or a black plastic plate (reference numerals 4.1 and 4.2) in front thereof. A measurement was also carried out without simulation of a wall effect, see reference numeral 2. This measurement without the reproduction of a wall effect (reference numeral 2) has the same value on the y-axis as the corrected mean value $MW_{kor}$. The stainless steel plates 3.1 and 3.2 or the black plastic plates 4.1 and 4.2 have been held at various distances in front of the turbidity sensor, which is why two different values result.

Thus, on the y-axis, the mean value MW is also plotted, or in other words, the characteristic noise expected for the respective ambient condition. However, the actual measured value of the noise parameter RK or the corrected mean value $MW_{kor}$ approximately constant. Therefore, there is a difference between the mean value MW and corrected mean value $MW_{kor}$ in FIG. 2, reference numerals 3.1, 3.2, 4.1 and 4.2.

A user can identify an appropriate ambient condition, such as material, diameter, surface roughness, surface color, surface texture and/or deposits at the container, and/or distance between sensor and container, and it is possible to carry out a corresponding compensation. This helps in avoiding incorrect measurements. The corresponding assignments of the type of interference to the predicted value of the noise parameter may be stored in the form of tables, as a function, formula, diagram or the like, for example on a memory in the higher-level unit. The appropriate ambient conditions are selected by the user, for example through the higher-level unit.

Figure 4:
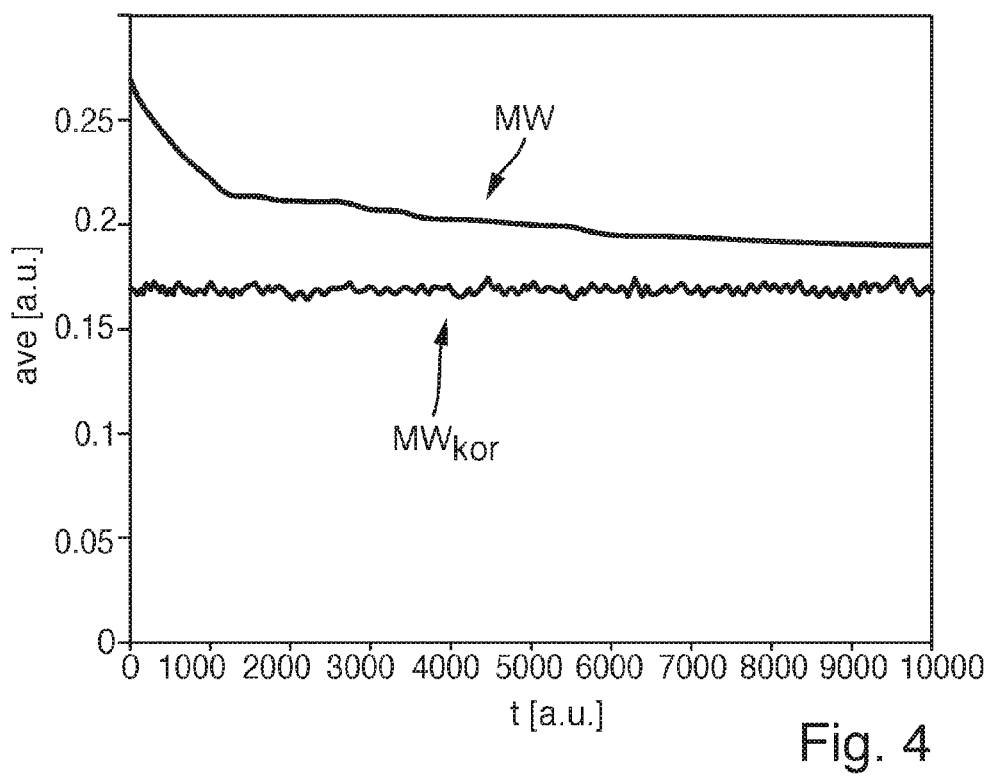
FIG. 4 is a chronological sequence of the determined and expected noise parameter in case of a soiled optical window of a turbidity sensor.

Alternatively or in addition, an automatic detection of the corresponding fault can be performed. As shown in FIGS. 3 and 4 and mentioned above, any interference has a predicted characteristic noise, so that the type of interference can be detected by measuring the noise parameter. The user can view the noise parameter on a display, for example at the transmitter. A message about the type of interference, i.e. the relevant ambient condition or the sensor status can also be displayed.

FIG. 4 shows the case of how the contamination of a window can be detected and compensated for. Here, a layer of grease was applied to an optical window, wherein the grease was removed slowly but not completely during the measurement, which you can see in FIG. 4, showing the mean value MW and the corrected mean value $MW_{kor}$.

Thus, the state of the sensor, namely the surface texture, deposits, contamination of the sensor, can also be detected and compensated for, and adjusted, if necessary.

The invention claimed is:

1. A method for determining the turbidity of a medium using at least one turbidity sensor for use in process automation, the method comprising:
    calculating parameters for a noise model for the turbidity sensor;
    passing transmitted radiation into a medium, wherein the transmitted radiation is converted into received radiation by scattering as a function of turbidity in the medium;
    converting the received radiation into a scattered light intensity;
    measuring a chronological sequence of the scattered light intensity;
    calculating a mean value of the chronological sequence of the scattered light intensity;
    calculating a turbidity value from the mean value using a calibration model;
    calculating a noise parameter based on the chronological sequence of the scattered light intensity;
    calculating a corrected mean value of the chronological sequence of the scattered light intensity using the noise parameter and the noise model;
    calculating a corrected turbidity value using at least the corrected mean value and the calibration model;
    calculating a turbidity offset by comparing the turbidity value and the corrected turbidity value; and
    determining whether the turbidity offset exceeds a threshold, wherein upon determining that the turbidity offset exceeds the threshold, generating a message indicating that the turbidity value contains interference due to an interference variable or an interference source.

2. The method according to claim 1, wherein:
    the corrected turbidity value is calculated using at least the corrected mean value, the mean value, and the calibration model.

3. The method according to claim 1, further comprising:
    upon determining that the turbidity offset exceeds the threshold, compensating the turbidity by determining an actual turbidity using the corrected turbidity.

4. The method according to claim 1, wherein the noise parameter is calculated using a Fourier transformation of the chronological sequence of the scattered light intensity.

5. The method according to claim 1, wherein:
    the corrected mean value is determined from the noise parameter using the noise model, the noise model defined as, $$RK = \alpha^* \sqrt{MW_{kor}} + \beta$$

where RK is the noise parameter, α is a scaling factor for the conversion of an electrical variable to the turbidity, $MW_{kor}$ is the corrected mean value, and β is a constant for the turbidity sensor.

6. The method according to claim 1, wherein:
said noise parameter depends on ambient conditions and/or the state of the turbidity sensor.

7. The method according to claim 6, wherein:
the ambient conditions are at least materials, diameter, surface roughness, surface color, surface texture and/or deposits on the container, and/or distance of turbidity sensor to the container.

8. The method according to claim 6, wherein:
the state of the turbidity sensor is surface texture, deposits, wear of an optical window, and/or contamination at the turbidity sensor.

9. The method according to claim 6, further comprising the step of:
displaying said noise parameter and/or a message about the ambient condition and/or state of the turbidity sensor.

10. A turbidity device comprising a turbidity sensor and a controller, the turbidity sensor configured to transmit radiation into a medium and to receive radiation scattered by turbidity in the medium, the controller configured to:
convert the received radiation into a scattered light intensity;
measure a chronological sequence of the scattered light intensity;
calculate a mean value of the chronological sequence of the scattered light intensity;
calculate a turbidity value from the mean value using a calibration model;
calculate a noise parameter based on the chronological sequence of the scattered light intensity;
calculate a corrected mean value of the chronological sequence of the scattered light intensity using the noise parameter and a noise model;
calculate a corrected turbidity value using at least the corrected mean value and the calibration model;
calculate a turbidity offset by comparing the turbidity value and the corrected turbidity value; and
determine whether the turbidity offset exceeds a threshold, wherein upon determining that the turbidity offset exceeds the threshold, generate a message indicating that the turbidity value contains interference through an interference variable or an interference source.

11. The turbidity device according to claim 10, wherein:
the turbidity device comprises a higher-level unit, which determines said noise parameter, the mean value, the corrected mean value, the turbidity and/or the corrected turbidity and performs a comparison of the turbidity with the corrected turbidity, wherein the higher-level unit is part of the turbidity device or is installed in an external device, in particular a transmitter.

12. The turbidity device according to claim 11, wherein:
the turbidity device is connected with the external device, in particular the transmitter, over an electrically insulated, and in particular,
inductive interface, or the turbidity sensor is connected with the external device, in particular the transmitter, over a wireless, in particular a Bluetooth interface.

13. The method according to claim 1, wherein the noise parameter is calculated using a standard deviation analysis of the chronological sequence of the scattered light intensity.

14. The method according to claim 1, wherein the calibration model outputs the turbidity value based on the mean value.

* * * * *